United States Patent [19]

Kötzsch et al.

[11] Patent Number: 4,467,105

[45] Date of Patent: Aug. 21, 1984

[54] METHOD OF PREPARING GLYCOL ESTERS OF ORGANOSILANES

[75] Inventors: Hans-Joachim Kötzsch, Rheinfelden; Hans-Joachim Vahlensieck, Wehr, both of Fed. Rep. of Germany

[73] Assignee: Dynamit Nobel Aktiengesellschaft, Troisdorf, Fed. Rep. of Germany

[21] Appl. No.: 422,612

[22] Filed: Sep. 24, 1982

[30] Foreign Application Priority Data

Sep. 30, 1981 [DE] Fed. Rep. of Germany ....... 3138835

[51] Int. Cl.³ .............................. C07F 7/04; C07F 7/18; C07F 7/08
[52] U.S. Cl. ....................................... 556/444; 556/446
[58] Field of Search ................................ 556/444, 446

[56] References Cited

U.S. PATENT DOCUMENTS

| | | | |
|---|---|---|---|
| 4,051,053 | 9/1977 | Elliott et al. | 556/446 X |
| 4,093,554 | 6/1978 | Jayne et al. | 556/444 X |
| 4,097,406 | 6/1978 | Scott et al. | 556/446 X |
| 4,172,186 | 10/1979 | Scott et al. | 556/446 X |

*Primary Examiner*—Paul F. Shaver
*Attorney, Agent, or Firm*—Felfe & Lynch

[57] ABSTRACT

The present invention relates to a method of preparing dimeric or polymeric organosilane esters whose ester component is at least one glycol moiety and whose silicon atoms are linked together by a glycol moiety. These compounds are known and are used as hydraulic fluids whose preparation involves considerable difficulty. The present invention avoids these difficulties by setting out from organosilane diglycol esters or triglycol esters and transposing them with diglycols or polyglycols. In this transposition the glycol ether corresponding to the glycols is formed and is removed by distillation. The degree of condensation of the organosilane ester products depends on the weight-ratio of the organosilane glycol ester to the diglycols or polyglycols.

7 Claims, No Drawings

METHOD OF PREPARING GLYCOL ESTERS OF ORGANOSILANES

BACKGROUND OF THE INVENTION

The subject matter of the present invention is a method for the preparation of glycol esters of organosilanes, in which at least two organosilicon groupings are linked together by a glycol or polyglycol moiety in the manner of an ester. The compounds are suitable as hydraulic fluids, heat carrier oils or system intermediates.

It is known, for example, from German Offenlegungsschrift No. 2,445,552 that a number of organosilane esters of mono- or polyfunctional organic hydroxy compounds in hydraulic oil formulations are a good guarantee of reliability and safety in hydraulically operated mechanical systems against very often life-threatening failures. This is due mostly to their water-binding properties, their compatibility with rubber and their heat-stability. They therefore constitute a considerable advance over the prior art.

The desire to employ these substances practically, however, has hitherto been thwarted by the fact that the production of these compounds on a large technical scale presents serious problems.

The above-mentioned compounds are essentially those of the formula

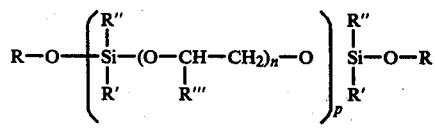

wherein

R is a glycol substituent of the general formula

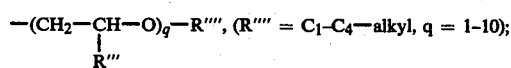

R'=RO— or a substituent from the group R'';
R''=alkyl ($C_1$-$C_{20}$), branched if desired, alkenyl, cycloalkyl or aryl;
R'''=H or $CH_3$;
n=1–12
p=0–10 (average degree of condensation),
and in some cases their branching products if R'=RO—.

For lack of any more practical method of procedure, the preparation of these very much sought-after products had to be performed in accordance with the above-mentioned patents, by partially esterifying a chlorosilane of the formula

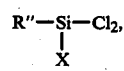

wherein X represents either chlorine or R' of the meaning given above, and R'' has the same meaning as above, in the presence of an amine (pyridine, for example) intercepting hydrogen chloride, with a glycol of the formula

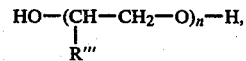

wherein R''' and n have the meaning given above, and then continuing and completing the esterification, also in the presence of an amine, with a glycol ether of the formula

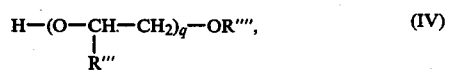

wherein R''', R'''' and q have the meaning given above. In some cases the two glycols could be used in reverse order. Towards the end of the reaction, the large and unusable amount of amine hydrochloride which necessarily had to form as a by-product had to be separated, and the large amount of solvent that had to be used on account of the great production of salt had to be removed by evaporation.

Lastly, then, the surplus of salt still dissolved in the product had to be removed by a complex refinement because it cannot be tolerated in hydraulic applications. The yields of this burdensome method of preparation in no case exceeded 70%. The disadvantages of this method of preparation—the only one available heretofore—are obvious.

To avoid the difficulties involved in the process described above, attempts have also been made to arrive at the desired products by the catalyzed or uncatalyzed transesterification of organosilane esters of the general formula

wherein Y represents a substituent R' in the meaning given above, or a substituent —OR'''', and R'''' also has the meaning given above, with glycols or glycol monoethers. These reactions, however, were very slow and incomplete. But it was regularly found that these processes of transesterification do not lead to the desired products but instead yield products of different composition. Especially the low alkoxy group is quite stubbornly retained, making the products unsuitable for hydraulic applications because their excessively low Gilpin vapor lock temperature impairs their ability to perform. These discouraging results suggested the conclusion that the transesterification approach is not promising, on account of the above-described disadvantages.

The problem therefore existed of finding a method of preparing the above-named glycol esters which does not have the burdensome disadvantages described above.

BRIEF SUMMARY OF THE INVENTION

As the solution to this problem, a method has been found which is characterized in that silicon esters of the general formula

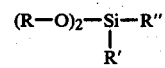

wherein R, R' and R" have the same meanings as above, are mixed with glycols of General Formula III in a ratio determined by the degree of condensation desired (p), at temperatures of 20° to 220° C., and then the glycol monoalkyl ethers of General Formula IV are removed by fractional distillation. The procedure of the invention is performed with surprising ease, without catalyst, and rapidly and completely yields the sought-after compounds of General Formula I, while the glycol ethers of General Formula IV which are displaced by the incorporation of the glycols of General Formula III are recovered by distillation. The ratio of compounds VI and III to one another is what determines the average degree of condensation p that is achieved in the Compound I prepared in accordance with the invention.

The molar ratio of the glycol ester VI to the alkylene glycol III is to amount to no more than 2:1. The greater the desired degree of condensation p is, the less is the amount of glycol ester VI that is required.

The yields of the method of the invention are virtually quantitative, and the products are usable directly and without further purification, and yet they will comply with the very high quality requirements of hydraulic oil formulations. Even when combined with the other conditioners used in these formulations, such as stabilizers for example, the products prepared by the method of the invention are compatible and present no problems.

Examples of substances prepared by the method of the invention are monomers and condensation products of:

of the glycol monoalkyl ether (IV) which is removed from the reaction mixture by distillation.

The preparation of the compounds of General Formula I by the method of the invention in a simple and effective manner is best accomplished by mixing the two starting substances III and VI in the ratio determined by the desired degree of condensation p, and the mixture is placed in the body of a good vacuum distillation column. There it is allowed to react at temperatures of up to 220° C., until the glycol has reacted with the silane esters (VI) to such an extent that at least a partial release of the glycol monoalkyl ether IV that forms in the reaction has taken place. The length of time will depend both on the temperature and on the compounds used. It is between approximately 50 minutes and 12 hours. Preferably the temperature is adjusted so that the distillation can begin after 2 to 4 hours have elapsed. The preferred temperatures are below the boiling points of the components involved, preferably between 90° and 160° C. Then the glycol monoalkyl ether of General Formula IV that has been displaced is fractionally distilled in such a manner that any remainder incompletely incorporated glycol of General Formula III do not pass over. This distillation can also be performed in vacuo.

For this method of distillation in accordance with the invention, high-vacuum stills of three and more theoretical trays have proven especially valuable. In a column of this kind, at the optimum vacuum, the product can be freed of any still volatile substances, to such an extent that it satisfies all quality requirements of the hydraulic 9,9,17,17-tetramethyl-2,5,8,10,13,16,18,21,24-nonaoxa-9,17-disilapentacosane of the structure $CH_3O(CH_2CH_2O)_2[Si(CH_3)_2(OCH_2CH_2)_2O]_1$ to $_{10}Si(CH_3)_2(OCH_2CH_2)_2OCH_3$, 12,12,23,23-tetramethyl-2,5,8,11,13,16,19,22,24,27,30,33-dodecaoxa-12,23-disilatetratriacontane of the structure $CH_3O(CH_2CH_2O)_3[Si(CH_3)_2(OCH_2CH_2)_3O]_1$ to $_{10}Si(CH_3)_2(OCH_2CH_2)_3OCH_3$, 15,15,29,29-tetramethyl-2,5,8,11,14,16,19,22,35,28,30,33,36,39,42-pentadecaoxa-15,29-disilatritetracontane of the structure:

$CH_3O(CH_2CH_2O)_4[Si(CH_3)_2(OCH_2CH_2)_4O]_1$ to $_{10}Si(CH_3)_2(OCH_2CH_2)_4OCH_3$, 3,6,9,13-tetramethyl-4,4,12,12-tetra-(2-ethoxypropoxy)-5,8,11-trioxa-4,12-disilapentadecane of the structure

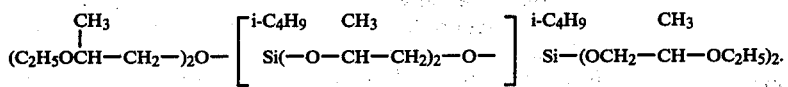

Suitable starting substances in accordance with General Formula VI are, for example, 9,9-dimethyl-2,5,8,10,13,16-hexaoxa-9-silaheptadecane, 15,15-dimethyl-2,5,8,11,14,16,19,22,25,28-decaoxa-15-silanonacosane, and ethyltris(2-ethoxypropoxy)-silane. These starting substances can be prepared simply in accordance with U.S. Pat. No. 4,228,092 from the corresponding chlorosilanes by direct esterification with the corresponding glycol monoethers, with the removal of hydrogen chloride.

Suitable condensation substances in accordance with General Formula II are, for example, ethylene glycol, triethylene glycol, polyethylene glycol 500, 1,2-propylene glycol, di-1,2-propylene glycol, tri-1,2-propylene glycol etc. It is desirable for the alkylene glycol (III) to have a boiling point that is higher than the boiling point fluid art. If desired, the quality can be further improved by additional concentration in a short-cut distillation or in a falling film or thin layer evaporator.

Glycol organosilane esters of General Formula I synthesized in this elegant manner by the method of the invention are suitable not only as hydraulic oil, in combination, if desired, with conditioners such as stabilizers and anticorrosive additives, but also as an improving additive in other hydraulic formulations. Furthermore, on account of their relatively high heat capacity, they are also suitable as agents for the transfer of heat. Due to their extraordinary thermal stability, they have a considerable life in closed heat transfer circuits, even at working temperatures around 340° C. Their very good compatibility with conditioners also make them suitable for use as aids in combining substances which are not miscible with one another; for example, chloroparaffins are miscible with silicone oils in the presence of the substances prepared in accordance with the invention.

Example

The two cubic meter boiler of a Sulzer column of approximately eight theoretical plates was charged with 330 kg (2.2 kmol) of triethylene glycol and 1538 kg (4 kmol) of 12,12-dimethyl-2,5,8,11,13,16,19,22-octaoxa-12-silatricosane ($BP_{0.1}$ 184° C.; $D_4^{20}$ 1.0396) and heated for 3 hours at 128° C. Then, at a reflux ratio of 5, and the boiler temperature rising slowly to 202° C., at a vacuum of 0.6 mbar and 88° C. top temperature, 716 kg of triethylene glycol monomethyl ether of a reusable, high purity, was distilled off over a period of approximate 5 hours. Then the vacuum was lowered over a period of about 15 minutes to 0.02 mbar, whereupon an additional 22 kg of distillate was obtained, which contained a small amount of starting ester plus additional ethylene glycol monomethyl ether. Finally the vacuum was relieved with dry nitrogen. 1130 kg of a clear, colorless product (yield, about 99%) of the structure:

$CH_3O(CH_2CH_2O)_3[Si(CH_3)_2(OCH_2CH_2)_3O]_pSi(CH_3)_2(OCH_2CH_2)_3OCH_3$ with the value of p between 1.2 and 1.6 was withdrawn from the body of the column.

The product has a silicon content of 9.86%. The density amounts to $D_4^{20}=1.057$.

The viscosities measured were:

3.65 mPa.sec (95° C.)
11.75 mPa.sec (38° C.) and
990.44 mPa.sec ($-40$° C.).

The boiling point at standard pressure was 377° C. The flash point was at 223° C.

It will be understood that the specification and examples are illustrative but not limitative of the present invention and that other embodiments within the spirit and scope of the invention will suggest themselves to those skilled in the art.

What is claimed is:

1. A process for the preparation of an organosilane ester of a polyol of the formula

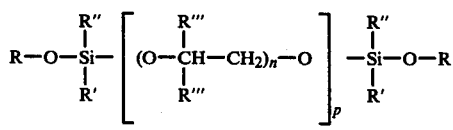

wherein
R = a glycol substituent of the general formula

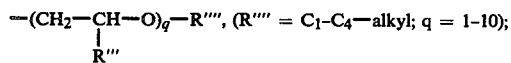

$R' = RO-$ or a substituent from group $R''$;
$R'' =$ alkyl ($C_1-C_{20}$), branched or unbranched, alkenyl, cycloalkyl or aryl;
$R''' = H$ or $CH_3$;
$n = 1-12$;
$p = 0-10$ (average degree of condensation) and branched products thereof when $R' = RO-$,
comprising the steps of mixing silicon esters of the general formula

wherein R, R' and R'' have the meanings given above with glycols of the general formula

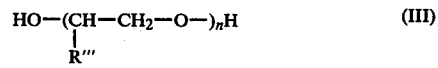

in a ratio predetermined by the selected condensation degree p, at temperatures of 20° to 220° C., allowing the resulting reaction mixture to react; and removing, from the reaction mixture, the glycol monoalkyl ethers of the general formula

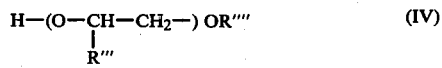

which are formed.

2. The process of claim 1, wherein the reaction mixture is reacted for up to 12 hours prior to removing the glycol monoalkyl ether.

3. The process of claim 1 or 2 wherein the reaction mixture is maintained at a temperature between about 90° and 160° C. during the reaction time.

4. The process of claim 2 wherein the reaction mixture is reacted for about 2 to 4 hours.

5. The process of claim 1 wherein the reaction mixture is maintained at a temperature of between 90° C. and 220° C.

6. The process of claim 1 wherein the monoalkyl ethers are removed by fractional distillation.

7. The process of claim 1 wherein triethylene glycol and 12, 12-dimethyl-2,5,8,11,13,16,19,22-octaoxo-12-silatricosane are mixed together in a molar ratio of approximately 1:2, heated for about 3 hours to a temperature of about 130° C.; and the impurities removed by fractional distillation to leave substantially pure $CH_3O(CH_2CH_2O)_3p$  $Si(CH_3)_2(OCH_2CH_2)_3OCH_3$ wherein p is 1.2 to 1.6.

* * * * *

UNITED STATES PATENT AND TRADEMARK OFFICE
CERTIFICATE OF CORRECTION

PATENT NO. : 4,467,105
DATED : August 21, 1984
INVENTOR(S) : Hans-Joachim Kötzsch et al.

It is certified that error appears in the above-identified patent and that said Letters Patent is hereby corrected as shown below:

Claim 7, line 2,    "octaoxo" should be -- octaoxa --.

Claim 7, line 7,    "$CH_3O(CH_2CH_2O)_{3p}Si(CH_3)_2(OCH_2CH_2)_3OCH_3$" should be -- $CH_3O(CH_2CH_2O)_3[Si(CH_3)_2(OCH_2CH_2)_3O]_p Si(CH_3)_2(OCH_2CH_2)_3OCH_3$ --.

Signed and Sealed this

Eighteenth Day of June 1985

[SEAL]

Attest:

DONALD J. QUIGG

Attesting Officer    Acting Commissioner of Patents and Trademarks